(12) United States Patent
Jun et al.

(10) Patent No.: US 12,390,402 B2
(45) Date of Patent: Aug. 19, 2025

(54) HIGH-CONTENT AND SUSTAINED-RELEASE RETINOID CAPSULE, AND COMPOSITION FOR REDUCING WRINKLES, CONTAINING SAME

(71) Applicant: LG HOUSEHOLD & HEALTH CARE LTD., Seoul (KR)

(72) Inventors: Seung-Hyun Jun, Seoul (KR); Byung-Jun Ahn, Seoul (KR); Hye-Jin Lee, Seoul (KR)

(73) Assignee: LG HOUSEHOLD & HEALTHCARE LTD., Seoul (KR)

( * ) Notice: Subject to any disclaimer, the term of this patent is extended or adjusted under 35 U.S.C. 154(b) by 811 days.

(21) Appl. No.: 17/311,129

(22) PCT Filed: Dec. 4, 2019

(86) PCT No.: PCT/KR2019/017040
§ 371 (c)(1),
(2) Date: Jun. 4, 2021

(87) PCT Pub. No.: WO2020/116940
PCT Pub. Date: Jun. 11, 2020

(65) Prior Publication Data
US 2022/0023164 A1 Jan. 27, 2022

(30) Foreign Application Priority Data
Dec. 4, 2018 (KR) .................. 10-2018-0154246

(51) Int. Cl.
| | |
|---|---|
| *A61K 8/11* | (2006.01) |
| *A61K 8/41* | (2006.01) |
| *A61K 8/67* | (2006.01) |
| *A61Q 19/08* | (2006.01) |

(52) U.S. Cl.
CPC .............. *A61K 8/11* (2013.01); *A61K 8/41* (2013.01); *A61K 8/671* (2013.01); *A61Q 19/08* (2013.01); *A61K 2800/56* (2013.01)

(58) Field of Classification Search
CPC . A61K 8/11; A61K 8/41; A61K 8/671; A61K 2800/56; A61Q 19/08
See application file for complete search history.

(56) References Cited

U.S. PATENT DOCUMENTS

| | | | |
|---|---|---|---|
| 5,851,538 A | 12/1998 | Froix et al. | |
| 6,162,448 A | 12/2000 | Nguyen et al. | |
| 6,344,206 B1 * | 2/2002 | Nguyen | A61K 47/34 424/59 |
| 2002/0035152 A1 | 3/2002 | Tong et al. | |
| 2003/0044469 A1 | 3/2003 | Petit et al. | |
| 2003/0232091 A1 | 12/2003 | Shefer et al. | |
| 2007/0196400 A1 | 8/2007 | Raschke et al. | |
| 2009/0181076 A1 | 7/2009 | Prestidge et al. | |
| 2012/0148669 A1 | 6/2012 | Benoit et al. | |
| 2015/0125520 A1 | 5/2015 | Mallard | |
| 2016/0303005 A1 | 10/2016 | Mallard et al. | |

FOREIGN PATENT DOCUMENTS

| | | | |
|---|---|---|---|
| CN | 105496801 A | 4/2016 | |
| EP | 2 108 361 A1 | 10/2009 | |
| WO | WO-2009111852 A2 * | 9/2009 | ............. A61K 31/07 |
| WO | WO-2016196664 A1 * | 12/2016 | ............. A61K 31/04 |

OTHER PUBLICATIONS

Machine translation of WO 2009/111852 A2 (Year: 2009).*
Mukherjee et al.; Retinoids in the treatment of skin aging: an overview of clinical efficacy and safety; Dove Medical Press Limited; Clinical Interventions in Aging 2006:1(4) 327-348 (Year: 2006).*
Vega et al.; Invited Review: Spray-Dried Dairy and Dairy-Like Emulsions—Compositional Considerations; American Dairy Science Association, 2006; J. Dairy Sci. 89:383-401 (Year: 2006).*
Millqvist-Fureby; Characterisation of spray-dried emulsions with mixed fat phases; Elsevier; Colloids and Surfaces B: Biointerfaces 31 (2003) 65-79 (Year: 2003).*
Ghasemiyeh et al.; Solid lipid nanoparticles and nanostructured lipid carriers as novel drug delivery systems: applications, advantages and disadvantages; Research in Pharmaceutical Sciences, Aug. 2018; 13(4): 288-303 (Year: 2018).*
Journal of Microencapsulation, "Development of a new solid lipid nanoparticle formulation containing retinoic acid for topical treatment of acne", Gisele A. Castro et al., vol. 24, No. 5, pp. 395-407 (Aug. 31, 2007).
Battaglia, "Lipid Nano- and Microparticles: An Overview of Patent-Related Research", Journal of Nanomaterials, 2019, vol. 2019, Article ID 2834941, 22 pages.
Kim et al., "Retinyl retinoate, a novel hybrid vitamin derivative, improves photoaged skin: a double-blind, randomized-controlled trial", Skin Research and Technology, 2011, vol. 17, pp. 380-385.
Mishra et al., "Solid Lipid Nanoparticles: Emerging Colloidal Nano Drug Delivery Systems", Pharmaceutics, 2018, vol. 10, p. 191—21 Pages.
Millqvist-Fureby, "Characterisation of spray-dried emulsions with mixed fat phases", Colloids and Surfaces B: Biointerfaces, 2003, vol. 31, pp. 65-79.
Muller et al., "Theory and Practice of Modern Drug Delivery Systems", People's Military Medical Press, 2004, pp. 250-253.

(Continued)

*Primary Examiner* — Robert A Wax
*Assistant Examiner* — John W Lippert, III
(74) *Attorney, Agent, or Firm* — Vorys, Sater, Seymour and Pease LLP; Mih Suhn Koh

(57) ABSTRACT

Provided is a composition for improving wrinkles including a high-content/sustained-release retinoid capsule. The high-content/sustained-release retinoid capsule according to the presently claimed subject matter can minimize skin side effects and maximize wrinkle improvement effects by significantly increasing the retinoid content in the capsule and stability and controlling the release rate.

8 Claims, 2 Drawing Sheets

(56) References Cited

OTHER PUBLICATIONS

Vega et al., "Invited Review: Spray-Dried Dairy and Dairy-Like Emulsions—Compositional Considerations", J. Dairy Sci., 2006, vol. 89, pp. 383-401.
Weisan, "Industrial Pharmacy", China Medical Science and Technology Press, 2010, pp. 484-485.
Zhang et al., "Preparation of Nanostructured Lipid Carriers Loaded with Retinoic Acid by the High Pressure Homogenization Method" The Chinese Journal of Process Engineering, 2005, vol. 5, No. 1, pp. 54-57.

* cited by examiner

[FIG. 1]
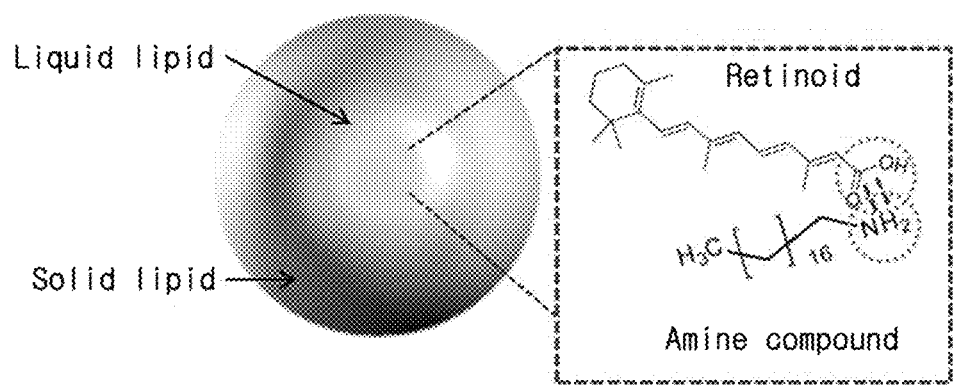
[FIG. 2]
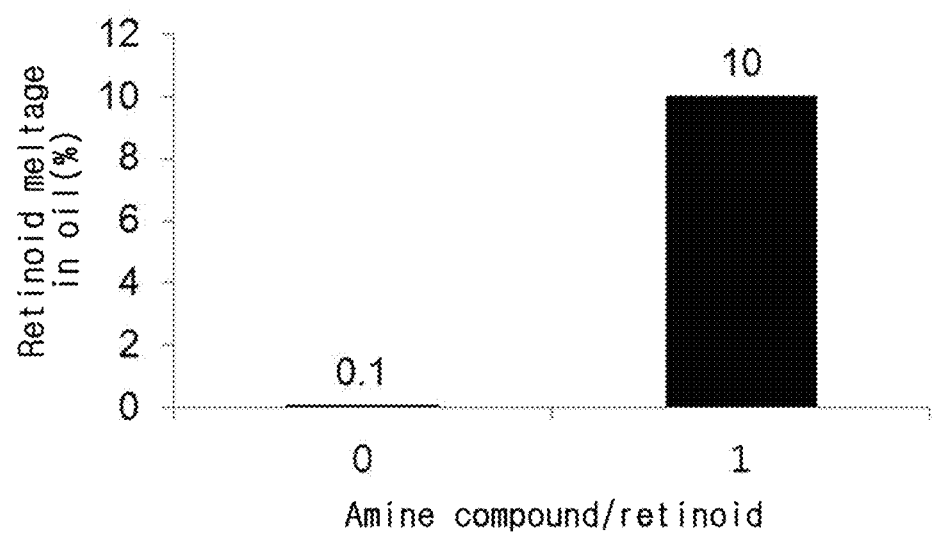

[FIG. 3]
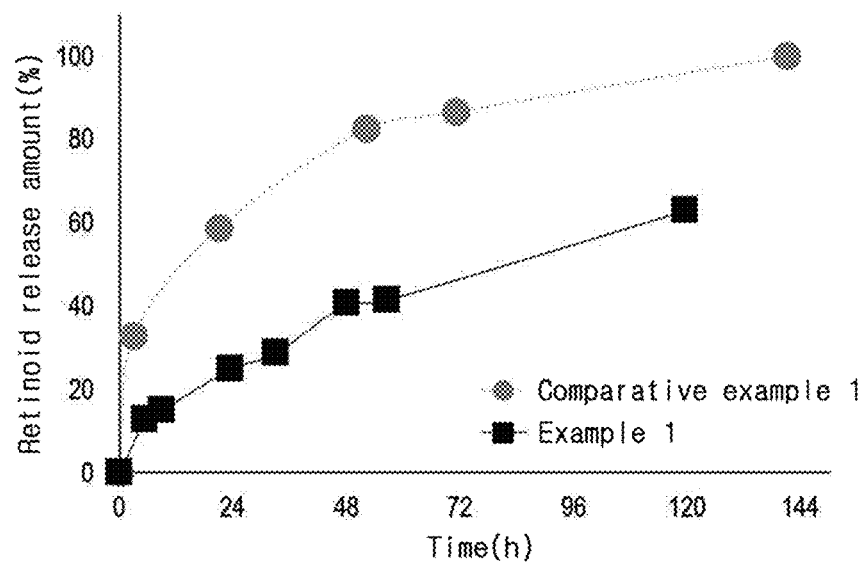
[FIG. 4]
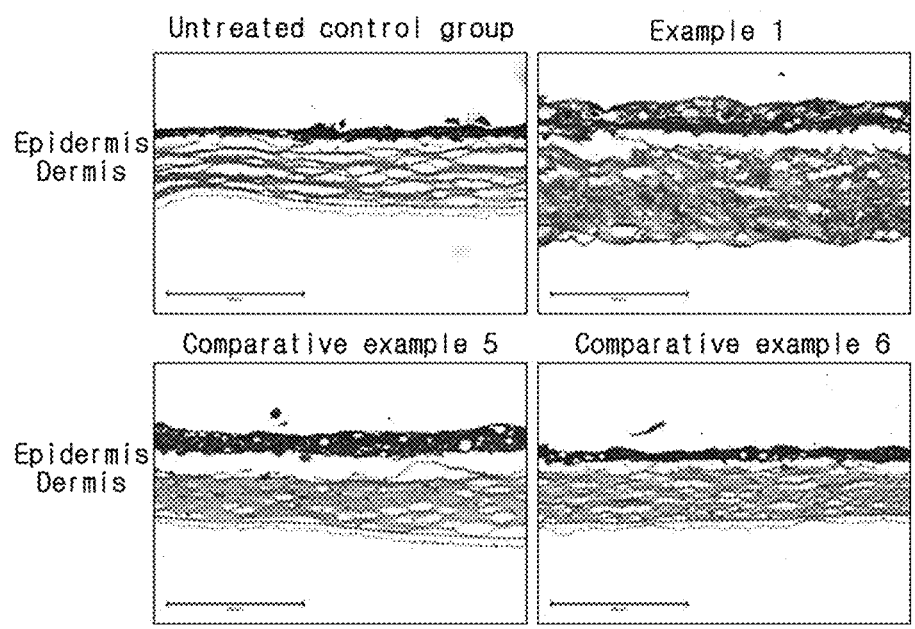

HIGH-CONTENT AND SUSTAINED-RELEASE RETINOID CAPSULE, AND COMPOSITION FOR REDUCING WRINKLES, CONTAINING SAME

TECHNICAL FIELD

The present application claims the priority based on Korean Patent Application No. 10-2018-0154246 filed on Dec. 4, 2018, and the entire contents disclosed in the description and drawings of the corresponding application are incorporated in the present application.

The present disclosure relates to a retinoid capsule and a composition for improving wrinkles comprising the same.

BACKGROUND ART

Skin aging is defined as any change in the skin integuments as a result of accumulation over years of gradual changes in its various constituents. Skin aging can be largely divided into photoaging due to ultraviolet rays and the like and natural aging resulting from accumulation over time.

The most representative change caused by aging is skin wrinkles. Skin wrinkles result in flattening of the epithelial and skin-epithelial junction, whereas in the dermis, collagen and elastin fiber produced by fibroblasts are gradually decreased by specific enzymes, resulting in overall reduction of extracellular matrix (ECM) associated with an increased destruction of said polymers.

Several specific compounds have already been identified as anti-wrinkle actives, and have been specifically used as a cosmetic composition for the purpose of preventing signs of skin aging, reducing and/or removing skin wrinkles.

Among them, 'retinoid' (retinol, retinal, retinoic acid, retinoid derivatives) is a substance proven to improved wrinkles in cosmetics and pharmaceuticals by improving the thickness of the epidermis and strengthening the ECM layer, and prescription medicine (retinoic acid) and cosmetics (retinol and retinoid derivatives) are widely used to improve wrinkles It has been known that the retinoid increase the epidermal thickness, reduce collagenase (MMP-1) in the dermis and increase collagen to improve wrinkles (See Table 1 below).

TABLE 1

|  | Effect | Side effects |
| --- | --- | --- |
| Corneum | — | Phototoxicity |
| Epidermis | Epidermal thickness ↑ (Improvement of fine wrinkles) | Dryness, pruritus peeing, erythema |
| Dermis | ECM ↑ MMP ↓ (Improvement of wrinkles) | — |

However, retinoid has side effects such as pruritus, burning sensation, erythema, peeling, and the like, and conjunctivitis may occur around eyes. In particular, it has been reported that retinoic acid-based substances such as tretinoin and tazarotene have more side effects due to the carboxyl group at the end of the retinoid. In addition, since the retinoid is easily photodegraded by exposure to air or light, its effect decreases over time and irritation caused by photodegraded retinoid become also a problem. Therefore, various methods for stabilizing retinoid have been reported. For example, Hydroxypinacolone Retinoate (HPR), Retinyl retinoate, and the like, in which the carboxyl group at the end of the retinoid is bound with other substances, have been reported and released as products (See Non-Patent Document, Skin Research and Technology 2011; 17: 380-385).

As another method, a method for encapsulating retinoid using various substances such as polymers, lipids, silica, and the like has been reported. However, in case of retinoic acid, the solubility in water or oil is very low, so the content of retinoic acid encapsulated in the actual capsule is very low at a level of 0.01% by weight based on the dry weight of the capsule. Furthermore, various patents for the retinoid capsule have been applied, but the actual solubility problem has not been overcome, so the actual content of retinoid in the capsule described in examples of these patents is very low (See Patent Documents 1, 2).

Patent document 1: Korean Patent Publication No. 10-2010-0003825
Patent document 2: Korean Patent Publication No. 10-2015-0093545

DISCLOSURE

Technical Problem

The present disclosure is to provide a high-content/sustained-release retinoid capsule that significantly increases the retinoid content in the capsule by significantly increasing the solubility of the retinoid, and reduces side effects and increases the epidermal thickness and the amount of dermal collagen, by increasing the stability of the ion-bonded retinoid and releasing it in way of sustained-release.

Technical Solution

As a means for solving the above problem, the present disclosure provides a retinoid capsule particle comprising a solid lipid shell; and a liquid lipid core, wherein the liquid lipid core comprises retinoid and an amine compound. In addition, the present disclosure provides a composition for improving wrinkles comprising the high-content/sustained-release retinoid capsule.

Conventional capsules comprising retinoid in solid lipids have very little retinoid content that can be contained to form capsules, but the present inventors have found that the retinoid content can be significantly increased to 20% by weight based on the total dry weight of the capsule and the retinoid capsule can has sustained-release property, when the retinoid capsule comprises a core shell structure in which the core has the retinoid comprised in the liquid lipid instead of the solid lipid and is surrounded with the solid lipid, thereby completing the present disclosure.

The method of the present disclosure can significantly increase the solubility by adding an amine compound to retinoid contained in the liquid lipid phase and significantly increase the retinoid content per capsule weight by containing retinoid in liquid lipid instead of solid lipid. In addition, it has been determined that the stability of retinoid can be significantly increased and the release rate can be reduced, by comprising retinoid ion-bonded with an amine compound in the liquid core located inside of this core-shell structure.

Consequently, as the result of applying the high-content/sustained-release retinoid capsule synthesized in this way to artificial skin, it has been confirmed that the effect for improving wrinkles is increased and the side effects (inflammation) are reduced, compared to conventional commercial retinoic acid ointment, and thereby it is confirmed that the capsule according to the invention can be used for a composition for improving wrinkles.

In the high-content/sustained-release retinoid capsule according to the present disclosure, the retinoid may be one or more selected from the group consisting of retinol, retinal, retinoic acid and a retinoid derivative. As the 'retinoid' available in the present disclosure, one or more kinds among retinol, retinal, retinyl palmitate, all trans retinoic acid, 9-cis retinoic acid, 13-cis retinoic acid and retinoid derivatives such as Etrtinate, Acitretine, Tazarotene, Adapalene, bexarotene and Seletinoid G may be selected, and preferably, all trans retinoic acid, 9-cis retinoic acid and 13-cis retinoic acid may be used. Most preferably, all trans retinoic acid may be used. In the high-content/sustained-release retinoid capsule according to the present disclosure, the amine compound means liposoluble amine having an amine group soluble in oil. The amine group refers to an organic compound and a functional group having an unshared electron pair on a nitrogen atom as a base. As the liposoluble amine, for example, one or more kinds of stearylamine, benethamine, hexylamine, heptyl amine, octylamine, chlorohexylamine, chloroheptylamine, chlorooxylamine and benzylamine may be selected, and preferably, stearylamine and benethamine may be used. The amount of the liposoluble amine is not limited as long as it can increase the solubility of retinoid in the liquid lipid. For example, about 0.1~100 moles, preferably, 0.2~50 moles, particularly, most preferably, 0.5~20 moles, for 1 mole of the retinoid raw material may be used.

The solid lipid comprised in the solid lipid shell may be one or more selected from the group consisting of glycerides (for example, monoglyceride, diglyceride, triglyceride, glyceryl behenate, etc.), fatty acids (for example, stearic acid, etc.), steroids (for example, cholesterol, etc.) and wax (for example, cetyl palmitate, etc.), but not limited thereto.

The liquid lipid comprised in the liquid lipid core may be for example, one or more kinds selected from the group consisting of caprylic/capryl triglyceride, glycerol with palmitic acid and/or stearic acid, mono-, di- and tri-ester, fatty acid ester with C1-C36-alkanol (cetyl palmitate, lanolin, isopropyl myristate, isopropyl stearate, oleic acid decyl ester, ethyl oleate, etc.) and plant oil (olive oil, caster oil, sesame oil, etc.), but not limited thereto.

In the high-content/sustained-release retinoid capsule according to the present disclosure, the lipid may comprise one or more fatty acid esters, i.e., a mixture of lipids comprising one or more fatty acid polyglycerides such as diglyceride and triglyceride based on a mixture of glycerides, and preferably comprising 30% by weight or more of caprylic acid and/or capric acid based on the total weight of the lipids.

According to one embodiment of the present disclosure, the lipid contents of the capsule is 15% by weight to 70% by weight, specifically, 20% by weight to 35% by weight, based on the total dry weight of the capsule. Moreover, the capsule may comprise a surfactant of 1% by weight to 60% by weight, preferably, 5% by weight to 40% by weight, when synthesized.

According to another embodiment of the present disclosure, the retinoid comprised in the capsule may be comprised as high content of 1% by weight or higher, 2% by weight or higher, 3% by weight or higher, 4% by weight or higher, 5% by weight or higher, 6% by weight or higher, 7% by weight or higher, 8% by weight or higher, 9% by weight or higher, 10% by weight or higher, 11% by weight or higher, 12% by weight or higher, 13% by weight or higher, 14% by weight or higher, 15% by weight or higher, 16% by weight or higher, 17% by weight or higher, 18% by weight or higher, 19% by weight or higher, or 20% by weight or higher, based on the dry weight of the retinoid capsule particle.

This high-content/sustained-release retinoid capsule according to the present disclosure may be produced by the method comprising emulsifying (i) a solid lipid phase, (ii) a liquid lipid phase comprising retinoid and an amine compound and (iii) an aqueous phase comprising a surfactant and water under the conditions of low pressure of 0.0005 atm to 0.5 atm, preferably, low pressure of 0.001 atm to 0.5 atm, and high temperature of 50° C. to 90° C.; obtaining a retinoid capsule formed by the emulsifying; washing the obtained retinoid capsule; and drying the washed retinoid capsule.

The present inventors have surprisingly found that the PDI value indicating the degree of dispersion become lower and the content of emulsifiers causing irritation can be reduced to less than half compared to the conventional one, when the retinoid capsule particle is synthesized through an emulsification process at low pressure and high temperature in this way. The PDI (Polydispersity Index) value is an index representing the particle width parameter (degree of dispersion) measured by a dynamic light scattering (DLS) equipment, and lower PDI value means that the distribution of the average particle size is lower, meaning that particles of more uniform size are synthesized.

As described above, when a retinoid capsule is produced at lower reaction pressure in the emulsification process for synthesizing a retinoid capsule, the capsule can be synthesized even when the emulsifier content comprised in the capsule is 20% by weight or less, 15% by weight or less, 10% by weight or less, or 5% by weight or less based on the dry weight of the retinoid capsule particle, and its particle uniformity has the remarkably improved PDI (Polydispersity Index) value of 0.3 or less, 0.2 or less, 0.1 or less, 0.05 or less, or 0.01 or less.

In addition, the present disclosure provides a composition for improving wrinkles comprising the retinoid capsule particle.

When the composition is used as a skin external application, it may further comprise a supplement commonly used in the skin science field such as a fat substance, an organic solvent, a dissolving agent, a concentrate and a gelling agent, a softener, an antioxidant, a suspending agent, a stabilizer, a foaming agent, an aromatic, a surfactant, water, an ionic or non-ionic emulsifier, a filler, a metal ion blocker and a chelating agent, a preservative, a vitamin, a blocking agent, a wetting agent, an essential oil, a dye, a pigment, a hydrophilic or hydrophobic activator, a lipid follicle or any other component commonly used for skin external application. In addition, the components may be introduced in an amount commonly used in the skin science field.

When the composition for improving wrinkles comprising a retinoid capsule particle is provided as a skin external formulation, it is not limited thereto, but it may have a formulation such as an ointment, a patch, a gel, cream or aerosol.

In addition, the composition for improving wrinkles comprising a retinoid capsule particle of the present disclosure may be provided in a cosmetic formulation. When the composition is used as a cosmetic, it may be prepared in a form of common emulsified formulation and solubilized formulation. For example, it may have a formulation such as cosmetic water as softening cosmetic water or nutrition cosmetic water, etc., emulsion as facial lotion, body lotion, etc., cream as nutrition cream, moisture cream, eye cream, etc., essence, cosmetic ointment, spray, gel, pack, sun screen, makeup base, a liquid type, solid type or spray type of foundation, powder, makeup removal as cleansing cream, cleansing lotion or cleansing oil, and a cleaning agent as cleansing foam, soap, body wash, etc., and the like.

Furthermore, the cosmetic may contain a supplement commonly used in the cosmetic field such as a fat substance, an organic solvent, a dissolving agent, a concentrate and a gelling agent, a softener, an antioxidant, a suspending agent, a stabilizer, a foaming agent, an aromatic, a surfactant, water, an ionic or non-ionic emulsifier, a filler, a metal ion blocker and a chelating agent, a preservative, a vitamin, a blocking agent, a wetting agent, an essential oil, a dye, a pigment, a hydrophilic or hydrophobic activator, a lipid follicle or any other component commonly used for cosmetics.

Advantageous Effects

The composition for improving wrinkles comprising a high-content/sustained-release retinoid capsule according to the present disclosure can be widely applied to cosmetics and pharmaceuticals for improving wrinkles by increasing the content and stability of the retinoid in the capsule and controlling the release rate to increase the effect for improving wrinkles while reducing side effects.

BRIEF DESCRIPTION OF THE DRAWINGS

FIG. 1 is a schematic diagram of the high-content/sustained-release retinoid.

FIG. 2 is the result of the solubility in oil according to the binding of an amine compound and retinoid.

FIG. 3 is the result of the release amount over time of Comparative example 1 and Example 1.

FIG. 4 is the result of confirming changes in the epidermis and dermis by cutting the cross section 3 days after applying Example 1, Comparative example 5 and Comparative example 6.

MODE FOR INVENTION

Hereinafter, the present disclosure will be described in more detail by examples. These examples are intended to illustrate the present disclosure more specifically, and it will be obvious for those skilled in the art that the scope of the present disclosure is not limited by these examples.

Example 1 is the high-content/sustained-release retinoid capsule.

Examples 2, 3 and 4 are the retinoid capsules synthesized by the emulsification process at low pressure and high temperature.

Comparative examples 1, 2 and 3 are the retinoid capsules not containing the amine compound.

Comparative example 4 is the untreated group (control group).

Comparative examples 5 and 6 are Stieve A which is a retinoic acid prescription medicine of 0.01% and 0.05%.

Comparative examples 7 and 8 are the retinoid capsules synthesized by the emulsification process at high pressure and high temperature.

EXAMPLES

I. Production of High-Content/Sustained-Release Retinoid Capsules

The composition of the retinoid capsules during synthesis included a solid lipid containing glycerol dibehenate and an amine compound (stearylamine); a liquid lipid containing caprylic/capryl triglyceride and an amine compound (stearylamine); and an aqueous solution containing a surfactant (Tween 60) and water (See Table 2; unit is % by weight). The retinoid was comprised in the liquid lipid and the solid lipid was heated to 70° C. and the liquid lipid was heated to 50° C., and a high temperature aqueous solution of the surfactant was mixed using a rotor-stator (Ultra-Turrax, Janke & Kunkel, Germany) at 8000 revolutions per minute for 2 minutes. The obtained capsules were homogenized with an ultrasonic generator and then the remaining surfactant was washed through centrifugation and then they were freeze-dried to complete. In Table 2 below, Example 1 is the high-content/sustained-release retinoid capsule and Comparative examples 1, 2 and 3 are the retinoid capsules not containing the amine compound.

TABLE 2

| Composition | Substance | Comparative example 1 | Comparative example 2 | Comparative example 3 | Example 1 |
|---|---|---|---|---|---|
| Solid lipid | Glycerol dibehenate | 4 | 4 | 4 | 3.7 |
|  | Stearylamine | 0 | 0 | 0 | 2 |
| Liquid lipid | Caprylic/capryl triglyceride | 2 | 2 | 2 | 3 |
|  | Stearylamine | 0 | 0 | 0 | 0.33 |
|  | Retinoic acid | 0.002 | 0.02 | 0.2 | 0.3 |
| Aqueous phase | Surfactant | 8 | 8 | 8 | 8 |
|  | Distilled water | up to 100 | up to 100 | up to 100 | up to 100 |
| Synthesis or not |  | ○ | X | X | ◉ |
| Dry weight of retinoid in the final capsule after washing (%) |  | 0.03 | — | — | 3 |

○: synthesized (PDI > 0.6)
X: not synthesized
◉: Uniformly synthesized (PDI < 0.6)

As shown in the Table 2, the maximum concentration of the retinoic acid soluble in the liquid lipid was 0.1% of the weight of the liquid lipid, and when added more the above, the retinoic acid was not dissolved, making it impossible to synthesize capsules (Comparative examples 1, 2, 3). On the other hand, it was determined that the solubility of retinoic acid was increased over 10% of the weight of the liquid lipid, when the amine compound at the same mole concentration as retinoic acid was added during dissolving retinoic acid in the liquid lipid (See Table 2). Through this, the dry weight of the retinoid in the final capsule after washing could be increased 100 times from conventional 0.03% to 3%.

II. Confirmation of Release Rate of High-Content/Sustained-Release Retinoid Capsules In order to compare the effect of the release rate of the retinoid capsules ion-bonded to the amine compound, Comparative example 1 and Example 1 were diluted to the same concentration, and then the supernatant was collected over time to confirm the release amount of retinoid. As a result, it was confirmed that the release rate was significantly reduced, compared to Comparative example 1 (See FIG. 3).

TABLE 3

|  | D50 | D70 | D80 | D90 |
|---|---|---|---|---|
| Comparative example 1 | 13.9 | 31.8 | 46.3 | 78.8 |
| Example 1 | 75.8 | 134.2 (Calc.) | 160 (Calc.) | 186 (Calc.) |

D: Time taken to release up to %

III. Confirmation of Effects of High-Content/Sustained-Release Retinoid Capsules In order to compare the effects of the high-content/sustained-release retinoid capsules, the degree of the effects and side effects were confirmed by applying 0.01% Example and the prescription medicine, Stieva A 0.01% and 0.05% (Comparative examples 5 and 6) using 3D skin (Tegoscience, Korea) consisting of epidermis and dermis, and then culturing it for 3 days and fractionizing skin. The thickness and area of the epidermis, and the collagen amount and density and collagenase yield as the effects, and the amount of Interleukin-1α that is an inflammatory marker as the side effects were confirmed.

As shown in Table 4 and FIG. 4, it was confirmed that all the indexes of the effects were significantly increased in case of Example 1, compared to Comparative example 4, and the inflammatory index was reduced. Moreover, it could be confirmed that the effects were increased more than Comparative examples 5 and 6 that are the prescription medicine at a high concentration.

TABLE 4

| | Effect index | | | | |
|---|---|---|---|---|---|
| | Epidermis | | Dermis Collagen amount and | Collagenase | Inflammatory index |
| Treatment method | Thickness | Area | density | (MMP-1) | Interleukin-1α |
| Comparative example4 | 100 | 100 | 100 | 100 | 100 |
| Example1 | 295 | 370 | 251 | 52 | 111 |
| Comparative example5 | 240 | 215 | 166 | 109 | 238 |
| Comparative example6 | 129 | 145 | 147 | 93 | 139 |

IV. Confirmation of Effects According to Reduction of Surfactant of High-Content/Sustained-Release Retinoid Capsules In Examples 2, 3 and 4, retinoid capsules were synthesized through the emulsification process at low pressure (0.05 atm) and high temperature (70~80° C.), and in Comparative examples 7 and 8, retinoid capsules were synthesized through the emulsification process at high pressure (1 atm) and high temperature (70~80° C.).

During synthesis of retinoid capsules, when the emulsification process was progressed at high pressure and high temperature, capsules were synthesized in case that the emulsifier content was 25% or higher of the total content excluding water (Table 5, Comparative example 7), and in case that the emulsifier content was reduced, when the temperature was lowered after emulsification, aggregation of lipid occurred and therefore capsules were not synthesized (Table 5, Comparative example 8). In addition, also in case that the emulsifier content was 25% or higher of the total content excluding water, a micrometer size of particles were included besides a nanometer size of particles and therefore polydisperse index (PDI) was not uniform. It was confirmed that during the emulsification process progressed in the present disclosure, when the emulsification was proceeded with the reduced pressure in the reactor, the synthesis of capsules was possible even when the emulsifier content was 10% or less of the total content excluding water, and uniform particles in the monodisperse form with the PDI value of 0.3 or less were formed.

The emulsifier is an element which can irritate the skin, and therefore, retinol capsules having reduced emulsifier content may reduce skin irritation. Through determining interleukin 1-a as an inflammatory index using cellular experiment, it was confirmed that in case of retinol capsules having reduced emulsifier content, the inflammatory index was reduced by more than 40% compared to the retinol capsules having the conventional emulsifier content.

TABLE 5

| Composition | Substance | Comparative example 7 | Comparative example 8 | Example 2 | Example 3 | Example 4 |
|---|---|---|---|---|---|---|
| Solid lipid | Glycerol dibehenate | 6 | 6 | 6 | 6 | 6 |
| | Stearylamine | 3 | 3 | 3 | 3 | 3 |
| Liquid lipid | Caprylic/capryl triglyceride | 5 | 5 | 5 | 5 | 5 |
| | Stearylamine | 1 | 1 | 1 | 1 | 1 |
| | Retinol | 2.5 | 2.5 | 2.5 | 2.5 | 2.5 |
| Aqueous phase | Surfactant | 6.5 | 3 | 6.5 | 3 | 1.5 |
| | Distilled water | up to 100 | up to 100 | up to 100 | up to 100 | up to 100 |
| Synthesis or not | | | X | ☺ | ☺ | ☺ |
| Dry weight of retinoid in the final capsule after washing (%) | | | — | 10.4 | 12.1 | 13.1 |
| Polydispersity index (PDI) | | 0.6 | X | 0.08 | 0.18 | 0.21 |

In the above, the applicant has described preferable examples of the present disclosure, but these examples are only one example which implements the technical spirit of the present disclosure, and any modification or alteration should be interpreted as belonging to the scope of the present disclosure as long as it implements the technical spirit of the present disclosure.

The invention claimed is:

1. A core-shell structured retinoid capsule particle comprising a solid lipid shell; and a liquid lipid core,
   wherein the liquid lipid core comprises a retinoid and an amine compound,
   wherein the amine compound is one or more selected from the group consisting of stearylamine, benethamine, hexylamine, heptylamine, octylamine, chlorohexylamine, chloroheptylamine, chlorooxylamine and benzylamine,
   wherein the amine compound is comprised both in the solid lipid shell and the liquid lipid core,
   wherein the content of the retinoid is 1 to 20% by weight based on the dry weight of the retinoid capsule particle, and the content of the amine compound is 0.2-50 moles per 1 mole of the retinoid, and
   wherein the retinoid capsule particle is synthesized by an emulsification process under the condition of low pressure of 0.001 to 0.5 atm and high temperature of 50 to 90° C.

2. The retinoid capsule particle according to claim 1, wherein the retinoid is one or more selected from the group consisting of retinol, retinal, retinoic acid and a retinoid derivative.

3. The retinoid capsule particle according to claim 1, wherein the retinoid is released from the retinoid capsule particle in a sustained manner.

4. The retinoid capsule particle according to claim 1, wherein the retinoid capsule particle has a Polydispersity Index (PDI) value of 0.3 or less, measured by using a dynamic light scattering (DLS) device.

5. A composition for improving wrinkles comprising the retinoid capsule particle according to claim 1.

6. The composition for improving wrinkles according to claim 5, wherein the composition is a cosmetic composition.

7. A method for improving skin wrinkles, comprising applying the cosmetic composition according to claim 6 to skin of a subject in need thereof.

8. The retinoid capsule particle according to claim 1, wherein the retinoid is ion-bonded with the amine compound.

* * * * *